US00PP17128P2

(12) United States Plant Patent
Cascante

(10) Patent No.: US PP17,128 P2
(45) Date of Patent: Oct. 3, 2006

(54) ***IMPATIENS* PLANT NAMED 'CAMEO BURGUNDY SURPRISE'**

(50) Latin Name: *Impatiens wallerana*
Varietal Denomination: Cameo Burgundy Surprise

(75) Inventor: Xenia Cascante, Alajuela (CR)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/177,591

(22) Filed: Jul. 8, 2005

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
*Assistant Examiner*—Louanne Krawczewicz Myers
(74) *Attorney, Agent, or Firm*—The Webb Law Firm

(57) ABSTRACT

'Cameo Burgundy Surprise' is a new variety of *impatiens* that exhibits full, double burgundy and white bi-colored flowers.

1 Drawing Sheet

Botanical classification: *Impatiens wallerana.*
Varietal denomination: 'Cameo Burgundy Surprise'.

BACKGROUND OF THE INVENTION

The present invention comprises a new and distinct cultivar of *Impatiens wallerana* known by the varietal name 'Cameo Burgundy Surprise' (breeder reference number IM12098). The new variety was discovered in Quebradilla, Cartago, Costa Rica. The new variety is the result of a cross between two unnamed, unpatented *Impatiens wallerana* plants.

The purpose of the breeding program was to develop a fully double-flowering cultivar that is compact, mounded, having good garden performance, and large burgundy and white bi-colored flowers. Comparisons between the new variety and its parents cannot be made, as the parental varieties no longer exist. The new variety is similar in plant shape to 'Cameo Scarlet Surprise' (U.S. Plant Pat. No. 14,598), but has rich burgundy in its petal color. The new variety was first asexually reproduced by stem tip cuttings in Quebradilla, Cartago, Costa Rica. The new variety has been trial and field tested and has been found to retain its distinctive characteristics and remain stable and true to type through successive propagations of asexual reproduction. Characteristics that distinguish the new variety from others known to the breeder include:

- Largest sized flower of the burgundy and white bi-color flowers of *Impatiens wallerana* known to the breeder;
- Compact, mounded growth habit with flowering over the top of the leaf canopy;
- Flowers tend to face upward;
- Self branching when propagated from a vegetative cutting;
- Flower remains full double, even when the plants are subjected to environmental stress like excessive drying, low levels of fertilizer and very high temperatures;
- Can be finished in 20 cm (3 plants) and 30 cm (5 plants) hanging baskets in 8–10 weeks and in 10 and 15 cm pots in 5–6 weeks;

- Compact, mounded growth habit under most growing conditions makes the new variety ideal for hanging baskets and large containers;
- Free from any major disease or insect problems;
- Distinct rounded leaf shape and somewhat larger mature leaf results in a dense foliated plant; and
- Can be grown at moderate levels of sunshine but requires some shade outdoors in the summer.

The new variety was grown in a 15 cm container in Lompoc, Calif. under Dynaglass with 30% shade and 21–24° C. day temperatures and 16–18° C. night temperatures. The new variety initiates roots in 10 days in the summer and 12 days in the winter at 21° C. The new variety exhibits developed roots at 21 days at an average temperature of 21° C. Its rooting habit is very dense, fibrous and freely branching with fine roots.

DESCRIPTION OF THE DRAWING

The accompanying photographic drawing illustrates the new variety, with the color being as nearly true as is possible with color illustrations of this type.

DESCRIPTION OF THE PLANT

Figure 1:
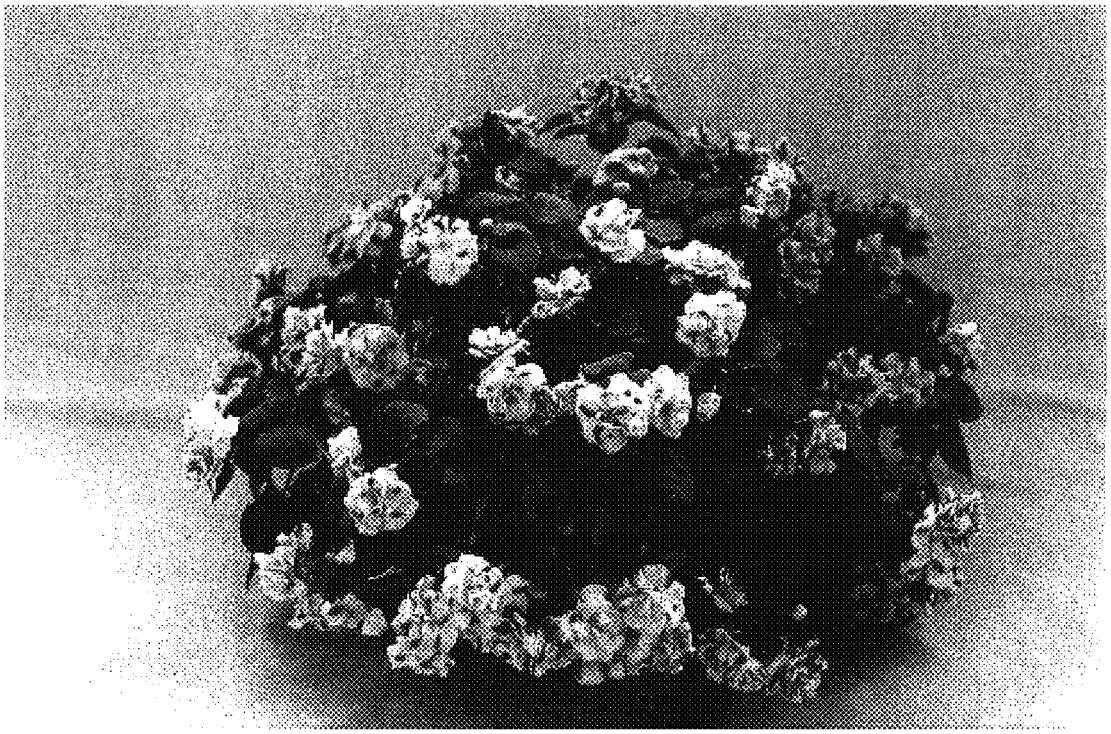

The following detailed description sets forth the characteristics of the new cultivar. The data which defines these characteristics were collected by asexual reproductions carried out in Lompoc, Calif. The color readings were taken indoors under 4000–5000 foot candles of light. The new variety was twelve weeks old when described. Color references are primarily to the 1966 R.H.S. Colour Chart of The Royal Horticultural Society of London.

PLANT

Form: Mounded; spreading.
Height (from soil to top of flowers): 14–16 cm.
Plant diameter: 20–25 cm.
Vigor: Vigorous, but not open or leggy.
Branching habit: Highly self-branched.

Lateral branches:
*Color.*—147C with heavy 184A & 184B on stem.
*Texture.*—Glabrous.
*Length.*—16–18 cm.
*Diameter.*—8–10 mm.
*Internode length.*—10–20 mm, but varies greatly due to location.
*Strength.*—Strong.
*Quantity.*—10 or more.

Foliage:
*Arrangement.*—Alternate.
*Number of leaves per stem.*—16 or more, but varies.
*Size of mature leaf.*—Length: 40–45 mm. Width: 20–40 mm.
*Shape of leaf* (*generally*).—Ovate.
*Shape of apex.*—Acute.
*Shape of base.*—Acute.
*Texture.*—Glabrous.
*Aspect.*—Upward facing.
*Margin type.*—Crenate with moderate lobing and finely ciliate.
*Fragrance.*—None.
*Color.*—Young leaves: Upper surface: 147A. Lower surface: 148B with faint areas of 185D. Mature leaves: Upper surface: 147A. Lower surface: 148B with faint areas of 185D.
*Petiole.*—Length: 10–12 mm, but variable. Diameter: 2 mm. Color: 147B with a heavy 185C cast. Texture: Glabrous. Veins: Venation pattern: Pinnate. Color: Upper surface: 147B. Lower surface: 146A.

FLOWER

Natural flowering season at specified location: Continuous under greenhouse conditions with no day length response.
Flower type and habit: Double with flowers above foliage. Petals self-cleaning.
Number of flowers per plant: 75–100 on mature plant.
Time of day of flower opening: Morning.
Fragrance: None.
Longevity on the plant: 5–7 days, but is greatly affected by the environment.
Flower height: 25 mm.
Flower diameter: 45 mm.

Bud:
*Stage of development when described.*—Mature.
*Shape.*—Ovate.
*Diameter.*—12 mm.
*Length.*—12–15 mm.
*Color.*—146D with 155B and 63B showing through.

Petals:
*Arrangement.*—Whorls of 5.
*Quantity.*—35–40 per flower.
*Length.*—22 mm (Note: Each whorl petal gets smaller).
*Width.*—20 mm (Note: Each whorl petal gets smaller).
*Shape.*—Heart to ovate.
*Apex.*—Rounded with some having indentations in the middle.
*Base.*—Acute.
*Margin.*—Entire.
*Texture.*—Smooth, glabrous.
*Color.*—When opening: All petals (upper surfaces): 57A & 155B with 62C blending between the two colors. All petals (lower surfaces): 57B & 155B with a trace of 62C at 57B edge. Fully opened: All petals (upper surfaces): 57A & 155B with larger areas of 62C. All petals (lower surfaces): 57B & 155B with larger areas of 62C.

Sepals:
*Number.*—5 (2 lower, 1 dorsal, and 2 lateral).
*Length.*—Lower: 6 mm. Dorsal: 18 mm. Lateral: 3 mm.
*Width.*—Lower: 5 mm. Dorsal: 20 mm. Lateral: 1 mm.
*Apex, lower and dorsal sepals.*—Rounded with a slight lobe (indentation) in the center. Lateral sepals: Acute.
*Base* (*all sepal types*).—Rounded.
*Margin* (*all sepal types*).—Entire.
*Upper surface color.*—Lower: 147D. Dorsal: 155C in the center of the sepal; 61B to the right and left of center. Lateral: 146B.
*Lower surface color.*—Lower: 147D. Dorsal: 146C in the center of the sepal; 155C to the immediate right and left of center; 58B to the far right and left of center. Lateral: 146B.

Spur:
*Quantity.*—1 per flower.
*Length.*—40 mm.
*Diameter at apex.*—Less than 1 mm.
*Diameter at flower.*—45 mm.
*Aspect.*—45° angle from peduncle.
*Color.*—146C.

Peduncles:
*Length.*—25–30 mm.
*Diameter.*—1 mm.
*Color.*—147C.
*Texture.*—Glabrous.
*Orientation.*—45° angle with the stem.
*Strength.*—Strong.

Disease/pest resistance: Resistant to Botrytis, mildew and Rhizoctonia; not resistant to insects.
Weather tolerance: Rain resistant, but does not tolerate strong winds well.
Lasting quality: On plant: 5–7 days — environment affects.
Seed production and description: Not applicable.
Fruit production and description: Not applicable.

REPRODUCTIVE ORGANS

None observed.

I claim:

1. A new and distinct variety of *Impatiens* plant, named 'Cameo Burgundy Surprise', as described and illustrated.

* * * * *